United States Patent [19]

Blount

[11] 4,088,632
[45] May 9, 1978

[54] PROCESS FOR THE PRODUCTION OF ACRYLATE SILICATE COMPOUNDS AND RESINOUS PRODUCTS

[76] Inventor: David H. Blount, 5450 Lea St., San Diego, Calif. 92105

[21] Appl. No.: 811,533

[22] Filed: Jun. 30, 1977

Related U.S. Application Data

[63] Continuation-in-part of Ser. No. 703,925, Jul. 9, 1976, abandoned.

[51] Int. Cl.$^2$ .......................... C08G 77/04; C07F 7/08
[52] U.S. Cl. .......................... 260/46.5 R; 260/448.2 R; 260/448.2 E; 260/448.2 Q; 260/46.5 UA; 260/448 LB; 260/46.5 Y
[58] Field of Search ................. 260/448.2 E, 448.2 R, 260/46.5 R, 448.2 Q, 46.5 UA, 448.2 B, 46.5 Y

[56] References Cited

U.S. PATENT DOCUMENTS 3,986,997  10/1976  Clark .......................... 260/448.2 E X

*Primary Examiner*—Paul F. Shaver

[57] ABSTRACT

A fine granular hydrated silica will react chemically with an organic acrylate by using an alkaline compound as a catalyst and by heating the mixture. The acrylate silicate compound is then polymerized with a catalyst such as a peroxide initiator.

12 Claims, No Drawings

PROCESS FOR THE PRODUCTION OF ACRYLATE SILICATE COMPOUNDS AND RESINOUS PRODUCTS

CROSS-REFERENCE TO RELATED CO-PENDING APPLICATION

This Application is a continuation-in-part of U.S. patent application Ser. No. 703,925, filed July 9, 1976, now abandoned.

BACKGROUND OF THE INVENTION

This invention relates to a process for the production of acrylate silicate compounds and resinous products by chemically reacting a hydrated silica ($SiO_2 \cdot xH_2O$) with an organic acrylate compound to produce an acrylate silicate compound. The acrylate silicate compound may then be polymerized with a catalyst such as a peroxide initiator.

The hydrated silica compound used in this process may be produced by the chemical reaction of a dry alkali metal metasilicate with a mineral acid or a hydrogen containing acid salt. The hydrated silica used in the following Examples were produced by reacting a dry granular alkali metal metasilicate with a hydrogen containing acid salt or a concentrated mineral acid. The white granular hydrated silica is washed with water, filtered, and then air dried at 25° to 75° C.

The hydrated silica reacts chemically with organic acrylate compounds, and when polymerized, it produces an acrylate silicate resinous product. The exact course of the reactions which take place during the process to produce acrylate silicate resinous products cannot be determined with 100% certainty. The hydrated silica appears to react with the acrylate compound by the process of alcoholysis.

The acrylate silicate compounds may be co-polymerized with other polymerable compounds such as acrylic acid compounds, vinyl monomers, organic dienes, organic allyl compounds, ethylene, propylene, and mixtures thereof.

The acrylate silicate resinous products produced in my process may be ground into a powder, softened with heat, and then molded into useful products. The acrylate silicate resinous products are soluble organic solvents and may be used as protective coatings on wood. They may be produced as an emulsion, or a dispersion in water and used as protective coatings on wood. The acrylate silicate compound may be co-polymerized with other organic polymerizable compounds and utilized as molding powder, and protective coatings on wood, metal, and plastic.

SUMMARY OF THE INVENTION

I have discovered that an organic acrylate compound will react chemically with a fine granular hydrated silica, in the presence of an alkali catalyst, to produce an acrylate silicate compound. The acrylate silicate compound may be polymerized with a catalyst such as a peroxide to produce an acrylate silicate resinous product. In the polymerization process, the hydrated silica apparently also acts as the cross-linking agent. Best results occur when about 1 mol of the hydrated silica is reacted with 1 or 2 mols of the organic acrylate compound.

Various organic acrylate compounds may be used in the process such as methyl methacrylate, ethyl acrylate, propyl acrylate, butyl acrylate, ethylene methacrylate, n-butyl methacrylate, ethyl methacrylate, polyethylene glycol dimethacrylate, tetraethylene glycol dimethacrylate, hexadecyl acrylate benzyl acrylate, cyclohexadecyl acrylate, methyl 2-chloroacrylate, 2-chloroethyl acrylate, 1,1-dihydroperfluorobutyl acrylate, lauryl acrylate, cyclohexylcyclohexyl methacrylate, allyl methacrylate, and mixtures thereof.

Various alkali compounds such as alkali metal carbonates, hydroxides, oxides, alkaline earth metal hydroxide, and alkali metal salts of weak acids may be used as the catalyst in the chemical reaction to produce acrylate silicate compounds and resinous products. Any strong alkali compound may be used as the catalyst such as alkali polysulfides and calcium carbide. The most useful alkali metal carbonate is sodium carbonate, but other alkali metal carbonates such as potassium carbonate may be used as the catalyst. Sodium hydroxide is the most useful alkali metal hydroxide, but potassium hydroxide and other alkali metal hydroxide may also be used as the alkali catalyse. Best results are obtained when the alkali catalyst is added in the amount of 5% to 20% of the weight of the reactants, hydrated silica, and the organic acrylate compound.

Various peroxide initiators may be used such as potassium persulfate, ammonium persulfate, hydrogen peroxide, cumene hydroperoxide, p-menthane hydroperoxide, potassium, or ammonium persulfate with ferric sulfate or cupric sulfate, and others. A redox system of initiation may be used. Benzoyl peroxide with a tertiary amine activator, such as N,N-dimethyl aniline may be used. Anionic agents will polymerize acrylate silicate compounds. Organic peroxide and hydroperoxides such as ethyl ketone peroxide with cobalt naphthenate, benzoyl peroxide, acetyl benzoyl peroxide, p-chlorobenzoyl peroxide, alkoxy benzoylperoxide, lauroryl peroxide, dibutyryl peroxide, dicaproyl peroxide, crotonyl peroxide, di-tert-alkyl peroxide, methyl amyl ketone peroxide, di-tert-butyl diphosphate peroxide, peracetic acid and cyclohexyl hypoperoxide.

The acrylate silicate compounds may be co-polymerized with various acrylic acids such as acrylic acid, methacrylic acid, ethyl acrylic acid, crotonic acid, chloroacrylic acid, fluroacrylic acid, cyclohexyl methacrylic acid, isobutyl methacrylic acid, and mixtures thereof.

The acrylate silicate compounds may be co-polymerized with various vinyl monomers such as styrene, acrylonitrile, vinyl chloride, vinyl acetate and mixtures thereof. They may be co-polymerized with various organic dienes such as butadiene, chloroprene and isoprene. They may be co-polymerized with various allyl compounds such as allyl alcohol and allyl chloride. They may be co-polymerized with various other compounds such as vinylidine chloride, 2-chloroethyl vinyl ether, allyl esters of dicarboxylic acids, allyl ethers of dihydric alcohols, aliphatic dichloroides, calcium carbide, chlorotrifluoroethylene, divinyl benzenes, propylene oxide, ethylene oxide, vinyl toluenes, N-vinyl carbazole, vinyl pyrolidone, methyl vinyl ketone, aryl vinyl ketones, alkyl vinyl ketones, acrylic aldehyde, methacrylonitrile, vinylidine cyanide, dichlorostyrene, bis (2-chloroethyl) ether, and mixtures thereof.

Any suitable modifying or additive compounds may be used in the reaction of this invention to vary the properties of the resinous product. Typical additives include aliphatic dihalides, maleic anhydride, polyester resins, polyether resins, polyurethane resins, sodium silicate, calcium hydroxide, sulfur, lead oxide, methacrylic anhydride, polysilicic acid esters, polybutenes, alkylated polystyrenes and mixtures thereof.

Any suitable emulsifier may be used in the reaction of this invention. Typical emulsifiers include sodium alkyl sulfates, soaps of fatty acids, anionic and cationic emulsifying agents, and mixtures thereof.

The acrylate silicate compounds are produced by chemically reacting the hydrated silica with an organic acrylate compound in the presence of a strong alkali catalyst before a polymerizing catalyst is added.

The preferred method of this invention is to mix the organic acrylate compound with a strong alkali catalyst in an aqueous solution, then add the fine, granular hydrated silica and heat the mixture at a temperature just below the boiling temperature of the mixture while agitating at ambient pressure for 10 to 30 minutes, thereby producing an acrylate silicate compound. Emulsifiers may be added to improve the mixing of the reagents. Peroxide catalyst is then added to the mixture and the temperature is kept between ambient temperature and 100° C while agitating at ambient pressure for 10 to 60 minutes, thereby producing an acrylate silicate resinous product. The reaction is complete in 12 to 24 hours.

The reactants may be mixed in any suitable proportions, depending upon the product characteristics desired. A catalytically effective amount of the selected alkali catalyst may be used. The reactions of this invention may take place under any suitable physical condition. While many of the reactions will take place acceptable at ambient temperature and pressures; in some cases, better results may be obtained at somewhat elevated temperatures and pressures. A pH of above 10 is preferred in this process.

In variation of the preferred process, all the reactants and catalyst may be mixed at the same time thereby producing an acrylate silicate resinous compound without going thru the steps to produce an acrylate silicate compound.

The primary object of the present invention is to produce acrylate silicate compounds and their resinous products. Another object is to produce acrylate silicate compounds that can be copolymerized with unsaturated organic chemicals to form new resins. Still another object is to produce acrylate silicate compounds and resinous products that are aqueous dispersions and may be painted on wood as protective coatings. Still another object is to produce acrylate silicate resinous products that are soluble in organic solvents and may be used for protective coatings on wood. Still another object is to produce acrylate resinous products which can be molded into useful products.

DESCRIPTION OF PREFERRED EMBODIMENTS

My invention will be illustrated in greater detail by the specific examples that follow; it being understood that those preferred embodiments are illustrative of, but not limited to, procedures which may be used in the production of acrylate silicate compounds and resinous products. Parts and percentages are by weight unless otherwise indicated.

EXAMPLE I

About 3 parts by weight of methyl methacrylate, 1 part by weight of sodium, 0.01 parts of soap and 10 parts by weight of water are mixed. 2 parts by weight of a fine granular hydrated silica are added than heated to 80° to 100° C while agitating at ambient pressure for 10 to 30 minutes thereby producing a mixture, methacrylic silicate, methyl methacrylate and hydrated silica.

About 0.01 parts by weight of potassium peroxide, and about 0.001 parts by weight of ferric sulfate are added to said mixture then heated to 80° to 100° C while agitating for 10 to 60 minutes thereby producing an emulsion of an acrylate silicate resinous product.

The acrylate silicate resinous product is coagulated by adding dilute mineral acid, hydrochloric acid, until the pH is about 7 to 8. The white resinous product is soluble in ethyl alcohol and isopropyl alcohol. The solution may be painted on wood and forms a tough protective coating. On filteration of the solution of the acrylate silicate resinous product and about 0.5 to 0.75 parts by weight of hydrated silica is filtered out unreacted with the methyl methacrylate.

EXAMPLE II

About 3 parts by weight of ethyl methacrylate, about 0.5 parts by weight of potassium hydroxide, 0.5 parts by weight of potassium carbonate, 0.01 parts by weight of soap and about 10 parts by weight of water are mixed then heated to 80° to 100° C while agitating for 10 to 15 minutes. About 2 parts by weight of dry fine granular hydrated silica are added then heated and agitated at ambient pressure for 10 to 30 minutes thereby producing a mixture of methacrylic silicate, ethyl methacrylate, and hydrated silica. About 0.01 to 0.02 parts by weight of ammonium persulfate and about 0.001 to 0.002 parts by weight of cupric sulfate are added to the mixture then heated to 80° to 100° C while agitating at ambient pressure for 10 to 60 minutes thereby producing an emulsion of an acrylate silicate resinous product.

The emulsion is coagulated by adding a hydrogen containing acid salt until the pH is about 7 to 8. The coagulated acrylate silicate resinous product will soften at 80° to 100° and may be molded into useful products.

EXAMPLE III

About 4 parts by weight of allyl methacrylate, 0.5 parts by weight of sodium hydroxide, 0.5 parts by weight of sodium carbonate, 15 parts by weight of water and 0.01 parts by weight of an emulsifier (sodium alkyl sulfate) are mixed. About 2 parts by weight of fine granular hydrated silica is added to the mixture then heated to 80° to 100° C while agitating at ambient pressure for 10 to 30 minutes. About 0.01 parts by weight of potassium persulfate and 0.001 parts by weight of ferric sulfate are added to the mixture and then the mixture is heated at 80° to 100° C while agitating for 10 to 60 minutes thereby producing an emulsion of an acrylate silicate resinous product.

The emulsion is coagulated by the addition of dilute sulfuric acid (3N). The acrylate silicate resinous product may be molded into useful products by heat and pressure.

EXAMPLE IV

About 4 parts by weight of cyclohexyl acrylate, 1 part by weight of potassium hydroxide, 0.01 parts by weight of soap, and 12 parts by weight of water are mixed then heated to 80° to 100° C for 10 to 15 minutes while agitating. About 2 parts by weight of fine granular hydrated silica is added to the mixture then heated to 80° to 100° C while agitating at ambient pressure for 10 to 30 minutes. Then 0.01 parts by weight of potassium persulfate and 0.001 parts by weight of ferric sulfate are added to the mixture then heated to 80° to 100° C for 10 to 60 minutes while agitating at ambient pressure, thereby producing an emulsion of an acrylate silicate resinous product.

Acetic acid is added to the emulsion to coagulate the acrylate silicate resinous product.

EXAMPLE V

About 3 parts by weight of methyl methacrylate, 0.01 parts by weight of an emulsifier, soap, 1 part by weight of sodium hydroxide, 15 parts by weight of water are mixed. About 2 parts by weight of dry fine granular hydrated silica are added to the mixture then heated to 80° to 100° C while agitating at ambient temperature for 10 to 30 minutes. About 1 part by weight of acrylic acid, 0.01 parts by weight of potassium sulfate and 0.002 parts by weight of cupric sulfate are added to the mixture then heated to 80° to 100° C while agitating for 10 to 60 minutes at ambient pressure thereby producing an emulsion of a copolymer of an acrylate silicate resinous product.

The emulsion of the copolymer is soluble when poured into a dilute solution of hydrochloric acid and may be coagulated from the acid by adding an alkali such as sodium carbonate until the pH is 7 to 8.

EXAMPLE VI

About 3 parts by weight of propyl acrylate, 0.005 to 0.02 parts by weight of a sodium alkyl sulfate, 1 part by weight of sodium hydroxide, and 15 parts by weight of water are mixed. About 2 parts by weight of a fine granular hydrated silica are added to the mixture then heated to 80° to 100° C while agitating for 10 to 30 minutes at ambient pressure. The evaporated water is replaced then 0.5 parts by weight of acrylic acid, 0.5 parts by weight of methacrylic acid, 0.01 parts by weight of hydrogen peroxide, 0.001 parts by weight of ferric sulfate, and 0.01 parts by weight of lauryl mercaptan are added to the mixture then heated to 80° to 100° C for 10 to 60 minutes thereby producing an emulsion of a copolymer of an acrylate silicate resinous product.

The emulsion will coagulate by adding a dilute mineral acid such as hydrochloric acid until the pH is 7 to 8.

The resinous product may be molded into useful objects by the use of heat and pressure.

EXAMPLE VII

About 3 parts by weight of methyl methacrylate, 0.01 parts by weight of soap, 1 part by weight of sodium hydroxide and 20 parts by weight of water are mixed. About 2 parts by weight of a dry fine granular hydrated silica are added to the mixture then heated to 80° to 100° C while agitating for 10 to 30 minutes at ambient pressure.

Although specific conditions and ingredients have been described in conjunction with the above Examples of preferred embodiments, these may be varied, and other reagents and additives may be used, where suitable, as described above, with similar results.

Other modifications and applications of this invention will occur to those skilled in the art upon reading this disclosure. These are intended to be included within the scope of this invention, as defined in the appended claims.

I claim:

1. The production of acrylate silicate resinous products by the following steps:
   (a) mixing about 3 to 4 parts by weight of an acrylate compound, 0.005 to 0.02 parts by weight of an emulsifier, and about 0.5 to 1 part by weight of an alkali catalyst in water;
   (b) adding about 2 parts by weight of a fine granular hydrated silica ($SiO_2 \cdot xH_2O$);
   (c) heating the mixture to 80° to 100° C while agitating at ambient pressure for 10 to 30 minutes;
   (d) adding a catalytic amount of a peroxide initiator;
   (e) heating the mixture to 80° to 100° C while agitating at ambient pressure for 10 to 60 minutes thereby
   (f) producing an emulsion of an acrylate silicate resinous product.

2. The process of claim 1 wherein the acrylate compound is selected from the group consisting of methyl methacrylate, ethyl methacrylate, allyl methacrylate, and mixtures thereof.

3. The method of claim 1 wherein the emulsifier is selected from the group consisting of soaps of fatty acids and sodium alkyl sulfate compounds.

4. The method of claim 1 wherein the alkali catalyst is selected from the alkali metal hydroxides consisting of sodium hydroxide and potassium hydroxide.

5. The method of claim 1 wherein the alkali catalyst is selected from the alkali metal carbonates consisting of sodium carbonate and potassium carbonate.

6. The method of claim 1 wherein the peroxide initiator is selected from the group consisting of hydrogen peroxide, potassium persulfate, ammonium persulfate, cumene hydroperoxide, benzoyl peroxide, ethyl ketone peroxide with cobalt naphthenate and O-menthane hydroperoxide.

7. The method of claim 1 wherein the peroxide initiator is potassium persulfate, 0.01 to 0.02 parts by weight, and ferric sulfate, 0.001 to 0.002 parts by weight.

8. The process of claim 1 wherein the peroxide initiator is utilized in a redox system, consisting of 10 to 15 parts by weight of water, 0.01 to 0.02 parts by weight of ammonium persulfate, about 0.001 to 0.002 parts by weight of cupric sulfate and about 0.01 to 0.02 parts by weight of sodium thiosulfate.

9. The process of claim 1 wherein an additional step of adding a dilute acid solution consisting of sulfuric acid, hydrochloric acid, acetic acid, sodium hydrogen sulfate and potassium hydrogen sulfate to the emulsion of the acrylate silicate resinous product until the pH is about 6 to 8 thereby coagulating the emulsion of acrylate silicate resinous product.

10. The process of claim 1 wherein an acrylic acid compound selected from the group consisting of acrylic acid, methacrylic acid, ethyl acrylic acid, and mixtures thereof are added in step (d) in the amount of 1 to 2 parts by weight thereby producing an emulsion of a copolymerized acrylate silicate product in step (f).

11. The product produced by the process of claim 1, acrylate silicate resinous product.

12. The product produced by the process of claim 10, an emulsion of a copolymerized acrylate silicate product.

* * * * *